(12) United States Patent
Dascalu

(10) Patent No.: US 9,649,336 B2
(45) Date of Patent: May 16, 2017

(54) COMPOSITIONS OF ALUMINUM FLUORIDE AND METHODS OF USE THEREOF FOR THE TREATMENT AND PREVENTION OF ACTINIC KERATOSIS AND SUN-INDUCED DAMAGES

(71) Applicant: Avi Dascalu, Tel-Aviv (IL)

(72) Inventor: Avi Dascalu, Tel-Aviv (IL)

( * ) Notice: Subject to any disclaimer, the term of this patent is extended or adjusted under 35 U.S.C. 154(b) by 0 days.

(21) Appl. No.: 14/651,287

(22) PCT Filed: Dec. 16, 2013

(86) PCT No.: PCT/IB2013/003230
§ 371 (c)(1),
(2) Date: Jun. 11, 2015

(87) PCT Pub. No.: WO2014/102619
PCT Pub. Date: Jul. 3, 2014

(65) Prior Publication Data
US 2015/0313936 A1    Nov. 5, 2015

Related U.S. Application Data

(60) Provisional application No. 61/745,646, filed on Dec. 24, 2012.

(51) Int. Cl.
| | |
|---|---|
| A61K 33/16 | (2006.01) |
| A61K 45/06 | (2006.01) |
| A61Q 17/04 | (2006.01) |
| A61K 8/26 | (2006.01) |
| A61K 9/00 | (2006.01) |
| A61K 47/10 | (2017.01) |
| A61K 47/14 | (2017.01) |
| A61K 47/20 | (2006.01) |

(52) U.S. Cl.
CPC ............... *A61K 33/16* (2013.01); *A61K 8/26* (2013.01); *A61K 9/0014* (2013.01); *A61K 45/06* (2013.01); *A61K 47/10* (2013.01); *A61K 47/14* (2013.01); *A61K 47/20* (2013.01); *A61Q 17/04* (2013.01)

(58) Field of Classification Search
CPC ........ A61K 33/16; A61K 8/26; A61K 9/0014; A61Q 17/04
See application file for complete search history.

(56) References Cited

U.S. PATENT DOCUMENTS

| | | | |
|---|---|---|---|
| 7,452,556 B2 | 11/2008 | Dascalu | |
| 2003/0170318 A1* | 9/2003 | Steiner | A61K 31/59 424/673 |
| 2007/0166255 A1* | 7/2007 | Gupta | A61K 8/31 424/70.1 |
| 2010/0266709 A1* | 10/2010 | Hicks | A61K 31/454 424/650 |

FOREIGN PATENT DOCUMENTS

| | | | |
|---|---|---|---|
| WO | WO 00/00159 | * | 1/2000 |
| WO | WO 0000159 | | 1/2000 |
| WO | WO 03028740 | | 4/2003 |

OTHER PUBLICATIONS

Chilvers, C. "Cancer mortality and fluoridation of water supplies in 35 US cities." *Int. J Epidemiol.* (1983) 12(4):397-404.
Kleerekoper, M. "Non-dental tissue effects of fluoride." *Adv Dent Res.*, (1994) 8(1):32-38.
Levy, M. et al. "Fluoride in drinking water and osterosarcoma incidence rates in the continental United States among children and adolescents." *Cancer Epidemiol* (2012) 36(2):e83-88.
Palmer, C.A. et al. "Position of Academy of Nutrition and Dietetics: the impact of fluoride on health." *J Acad Nutr Diet* (2012) 112(9):1443-1453.

* cited by examiner

*Primary Examiner* — Anna Falkowitz
(74) *Attorney, Agent, or Firm* — Marianne Fuierer; Moore & Van Allen, PLLC

(57) ABSTRACT

The present invention is directed to methods and compositions for the treatment or prevention of actinic keratosis and/or for countering the effects of skin aging and/or damage to blood vessels and fine wrinkling The present invention provides for a composition comprising aluminum fluoride or chemical compounds which releases aluminum fluoride to be used to treat or reduce the negative effects of actinic keratosis or sun-induced skin aging and associated conditions, for example, damaged blood vessels and fine wrinkling

13 Claims, 4 Drawing Sheets

COMPOSITIONS OF ALUMINUM FLUORIDE AND METHODS OF USE THEREOF FOR THE TREATMENT AND PREVENTION OF ACTINIC KERATOSIS AND SUN-INDUCED DAMAGES

RELATED APPLICATION

This application is filed under the provisions of 35 U.S.C. §371 and claims the priority of International Patent Application No. PCT/IB2013/003230 filed on Dec. 16, 2013 which in turn claims priority to U.S. Provisional Application No. 61/745,646 filed on Dec. 24, 2012, the contents of which are incorporated by reference herein for all purposes.

BACKGROUND OF THE INVENTION

Field of the Invention

The present invention is directed to the use of aluminum fluoride for the treatment and reduction of the effects of actinic keratosis and sun-induced damages.

Related Art in the Field

Actinic keratosis (AK), also known as solar keratosis, is a precancerous skin lesion that often appears as thick, scaly or crusty patches on an erythematous skin. These lesions of skin can eventually develop into erosions, plaques, ulcers and finally into skin carcinomas. Lesions associated with the condition usually range between 2 and 6 millimeters in size macroscopically. Actinic keratosis often affects the middle-aged or elderly, with Caucasian males between the ages of 65 and 74 having the greatest risk of developing actinic keratosis. However, in genetically sensitive individuals, the disease might start at the third to fourth decade (Andrews 2000). The anatomical basis of AK is related to clinical poikiloderma, a mixed skin disturbance related to skin thinning, proliferation and visualization of blood vessels, fine wrinkling and hyper or hypopigmentation.

Existing treatments of actinic keratosis (Fenske et al, 2010) include topical treatments using active ingredients such as:

5-Fluorouracil, a highly irritative and efficacious compound with about half of patients suffering from skin irritance;

Ingenol, a short term irritative treatment which is administered initially but without ability to control the dosing and a relatively weak results 6 months after treatment;

Tretinoin or retinoids, an adjunct to therapy which are less therapeutic, highly irritive and used for prevention;

Imiquimod, an immune response modulator. It is irritative, and only part of patients do respond to treatment with it;

Diclofenac, a non-steroidal anti-inflammatory which shows weak responses;

Mechanical treatments such as cryotherapy, surgical excisions, curettage or electrodesiccation to remove lesions associated with actinic keratosis but which do not control the disease, nor the exact area affected by the AK; and Photodynamic therapy to sensitize lesions to light by 5-aminolevulinic acid a relatively low efficacy treatment.

Therefore, there is a definitive need for the efficacious and convenient treatment of the AK precancerous lesions, wherein the new treatment does not suffers the disadvantages of previous treatments and is efficient, safe, non-toxic and non-irritative.

SUMMARY OF THE INVENTION

The present invention is directed to methods and compositions for treatment and prevention of actinic keratosis and for countering the effects of sun-induced damages and/or damage to blood vessels. The present invention is based, at least in part, on the discovery that a composition comprising aluminum fluoride can be used to treat or prevent actinic keratosis and its accompanying sun-induced damages and associated conditions, for example, proliferative blood vessels or fine wrinkling.

Accordingly, the present invention provides compositions for the treatment or prevention of actinic keratosis or sun-induced damage, comprising aluminum fluoride and methods for such treatment and prevention comprising administering said compositions to a subject.

In one aspect, the present invention is directed to a method for treating or reducing the negative effects of actinic keratosis in a subject by topically administering to the subject an effective amount of a composition comprising aluminum fluoride, a pharmaceutically acceptable salt thereof, or a combination of compounds which allow for the release of aluminum fluoride in vivo, thereby treating or preventing actinic keratosis in said subject. In one embodiment, the actinic keratosis is actinic cheilitis, inflammatory actinic keratosis, hypertrophic keratosis or pigmentary keratosis and the topical composition is applied to the surface of skin experiencing the negative effects of actinic keratosis.

In another aspect, the present invention provides for a composition including a single active agent, that being, the aluminum fluoride in said composition at a concentration of about 0.05% to about 2.00% w/w. Alternatively, the aluminum fluoride is present in said composition at a concentration selected from the group consisting of about 0.10% to about 0.75% w/w, about 0.25% to about 0.60% w/w, about 0.30% to about 0.55% w/w and preferably about 0.30% to about 0.45% w/w.

A still further aspect of the present invention provides for a method for treatment of actinic keratosis or sun damage comprising:

topically administering to an area of human skin affected by actinic keratosis or sun damage skin a topical dosage form comprising an aluminum fluoride based drug in a concentration of between about 0.10% and about 0.75% w/w; and continuing the administration until symptoms of actinic keratosis are abated.

Yet another aspect of the present invention provides for a composition comprising:

an aluminum fluoride based drug in a concentration of about 0.10% to about 0.75% w/w; and at least three of the following components selected from the group consisting of:

a. at least one emollient, such as lanolin, shea butter, glycerin and sorbitol, in a concentration of in a concentration of about 5% to about 60% w/w;

b. at least one thickener, such as castor oil or polyethylene, in a concentration of about 0.5% to about 20% w/w;

c. at least one preservative, such as paraben, in a concentration of about 0.01% to about 10% w/w;

d. at least one surfactant, such as, ammonium lauryl sulfate, cetylpyridinium chloride and cetyl alcohol, in a concentration of about 5% to about 25% w/w;

e. at least one antioxidant, such as, Vitamin C and E, in a concentration of about 0.01% to about 2% w/w; and f. water from about 2% to 80% w/w.

In another aspect, the present invention provides for a method of treating actinic keratosis or sun damage, the method comprising topically applying an aluminum fluoride composition to the affected area, the composition comprising:

a. an aluminum fluoride based drug in a concentration of about 0.25% to about 0.60% w/w and at least two of the following components selected from the group consisting of:
  i) at least one emollient in a concentration of in a concentration of about 5% to about 60% w/w;
  ii) at least one thickener in a concentration of about 0.5% to about 20% w/w;
  iii) at least one preservative in a concentration of about 0.01% to about 10% w/w;
  iv) at least one surfactant in a concentration of about 5% to about 25% w/w; and
  v) water from about 2% to 80% w/w.

In yet another aspect, the present invention provides for a composition comprising aluminum fluoride that is suitable for topical application including, for example, a gel, liquid or spray. Alternatively or in combination, the composition is a sustained release composition.

In a still further aspect, the present invention provides for a composition further comprising an inactive carrier including, but not limited to deionized water, arachidyl alcohol, behenyl alcohol, arachidyl glucoside, montanov 202, cetearyl alcohol, capric/caprilic triglyceride, isopropyl palmitate, steareth-2, dimethicon, steareth-20, allantoin, propylene glycol, methylisothiazolinone, Caprylic/Capric acids; medium chain triglycerides, PEG 400, PEG 3350, Pluronic F127, Polosamer F127, sodium benzoate, and combinations thereof.

In yet another aspect, the present invention provides for a method of treatment the present invention is directed to a method for treating or reducing the negative effects of actinic keratosis in a subject by topically administering to the subject an effective amount of a composition comprising aluminum fluoride, a pharmaceutically acceptable salt thereof, or a combination of compounds which allow for the release of aluminum fluoride in vivo, and further includes administering an additional agent selected from the group consisting of retinoids, an anti-inflammatory agent, a non-steroidal anti-inflammatory agent, imiquimod, diclofenac, 5-aminolevulinic acid, 5-fluorouracil and combinations thereof, wherein the addition agent may be administered simultaneously, before or after the administration of the aluminum fluoride compound.

In certain embodiments, the method further includes performing a procedure for removing a lesion or microerosion associated with actinic keratosis on said subject, wherein the removal procedure is selected from the group consisting of cryotherapy, excision, curettage, electrodesiccation, electrocautery, photodynamic therapy and laser therapy.

In one aspect, the composition is administered to said subject as related to its clinical response, i.e. preventively from once, twice or thrice weekly to at least once, twice, three times, four times or five times a day. In addition, the composition is administered to said subject over a period of 1 to 12 weeks. Additional preventive treatments may be carried out once-twice weekly as required by the clinical response. The effectiveness of treatment may be monitored, for example, by monitoring a lesion and/ or microerosion associated with actinic keratosis on the skin of said subject. The age of the subject is at least 30, 35, 40, 45, 50, 55, 60, 65 or 70 years old.

In another aspect, the present invention is directed to a method for treating, preventing or alleviating sun-induced damage and/or damage to blood vessels and collagen in a subject by administering to the subject an effective amount of a composition comprising aluminum fluoride, a pharmaceutically acceptable salt thereof, or a combination of compounds which allow for the release of aluminum fluoride in vivo, thereby treating, preventing or alleviating skin aging and/or damage to blood vessels and fine wrinkling in the subject. In a particular embodiment, the method further includes measuring skin pigmentation and/ or measuring skin vascularization in said subject.

In yet another aspect, the present invention is directed to a method for treating or preventing actinic keratosis in a subject by selecting a subject who is susceptible to the development of actinic keratosis and administering to said subject an effective amount of a composition comprising aluminum fluoride, a pharmaceutically acceptable salt thereof, or a combination of compounds to allow for the release of aluminum fluoride in vivo, thereby treating or preventing actinic keratosis in said subject. In various embodiments, the subject has type I or II skin (extremely susceptible to skin damage as well as cancers like basal cell carcinoma, squamous cell carcinoma and melanoma), and/or has a history of extensive exposure to the sun and/or ultraviolet irradiation.

In a further aspect, the present invention is directed to a composition including aluminum fluoride as the active agent, a pharmaceutically acceptable salt thereof, or a combination of compounds which allow for the release of aluminum fluoride in vivo in an amount effective for the treatment or prevention of actinic keratosis in a subject, and a carrier comprising at least two, three, four or five inactive ingredients selected from the group consisting of montanov 202, capric/caprilic triglyceride, isopropyl palmitate, methylisothiazolinone and sodium benzoate Caprylic/Capric acids; medium chain, triglycerides, PEG 400, PEG 3350, Poloxamer F127, Pluronic F127 and purified water.

In another aspect, the present invention is directed to a composition including aluminum fluoride, a pharmaceutically acceptable salt thereof, or a combination of compounds which allow for the release of aluminum fluoride in vivo, in an amount effective for the treatment or prevention of actinic keratosis in a subject and an additional agent selected from the group consisting of retinoids, an anti-inflammatory agent, a non-steroidal anti-inflammatory agent, imiquimod, diclofenac, a retinoid, 5-aminolevulinic, 5-fluorouracil, and combinations thereof.

In a still further aspect, the aluminum fluoride is present in the composition at a concentration of about 0.05% to about 2.00% w/w or, alternatively, at a concentration selected from the group consisting of about 0.10% to about 0.75% w/w, about 0.25% to about 0.60% w/w, about 0.30% to about 0.55% w/w and preferably about 0.30% to about 0.45% w/w.

In yet another aspect, the present invention provides for a composition that is suitable for topical application. For example, the composition may be in the form of a gel, liquid or spray. In addition, the composition may be a sustained release composition, for example, for release of the aluminum fluoride, a pharmaceutically acceptable salt thereof, or the combination of compounds for at least one, two, three, four, five or six weeks.

In a further aspect, the present invention provides for a composition that further comprises an inactive carrier, for example, deionized water, arachidyl alcohol, behenyl alcohol, arachidyl glucoside, montanov 202, cetearyl alcohol, capric/caprilic triglyceride, isopropyl palmitate, steareth-2, dimethicon, steareth-20, allantoin, propylene glycol, methylisothiazolinone, Caprylic/Capric acids; medium chain triglycerides, PEG 400, PEG 3350, Poloxamer F127, Pluronic F127, sodium benzoate, and combinations thereof. The composition may further comprise an additional agent selected from the group consisting of retinoids, an anti-inflammatory agent, a non-steroidal anti-inflammatory agent, imiquimod, diclofenac, 5-aminolevulinic acid, 5-fluorouracil, and combinations thereof.

In a further aspect, the present invention is directed to a composition including aluminum fluoride, a pharmaceutically acceptable salt thereof, or a combination of compounds which allow for the release of aluminum fluoride in vivo in an amount effective for the treatment, prevention or alleviation of skin aging and/or damage to blood vessels and collagen in a subject and a purified water carrier comprising at least two, three, four or five inactive ingredients selected from the group consisting of montanov 202, capric/caprilic triglyceride, isopropyl palmitate, methylisothiazolinone, Caprylic/Capric acids; medium chain, triglycerides, PEG 3350, PEG 400, Poloxamer F127, Pluronic F127, and sodium benzoate.

Other features and advantages of the invention will be apparent from the following detailed description and claims.

DETAILED DESCRIPTION OF THE INVENTION

Figure 1:
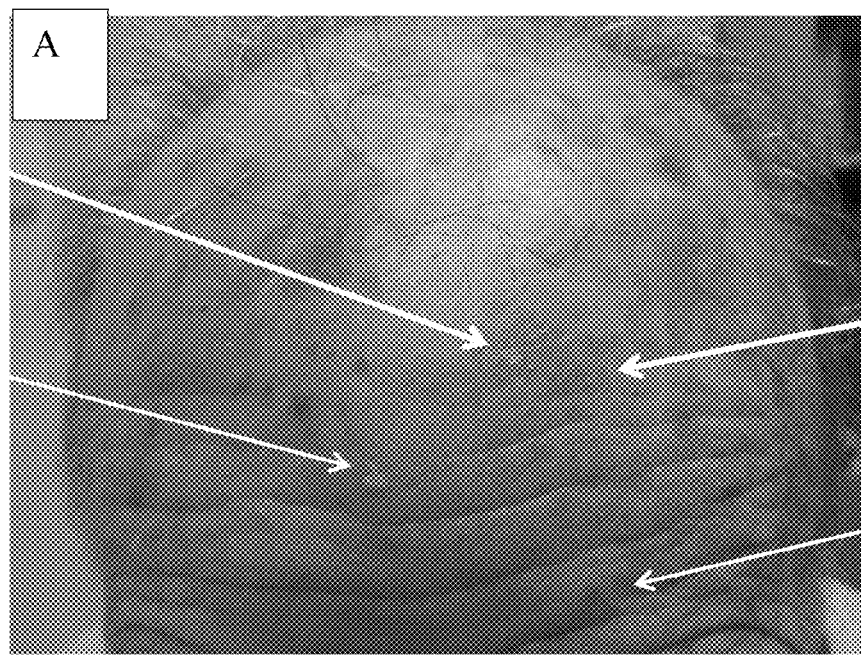
FIG. 1 shows the effects of using AlFl at a dose of about 0.30%, twice daily for three weeks wherein A is before and B is after.
Figure 1:
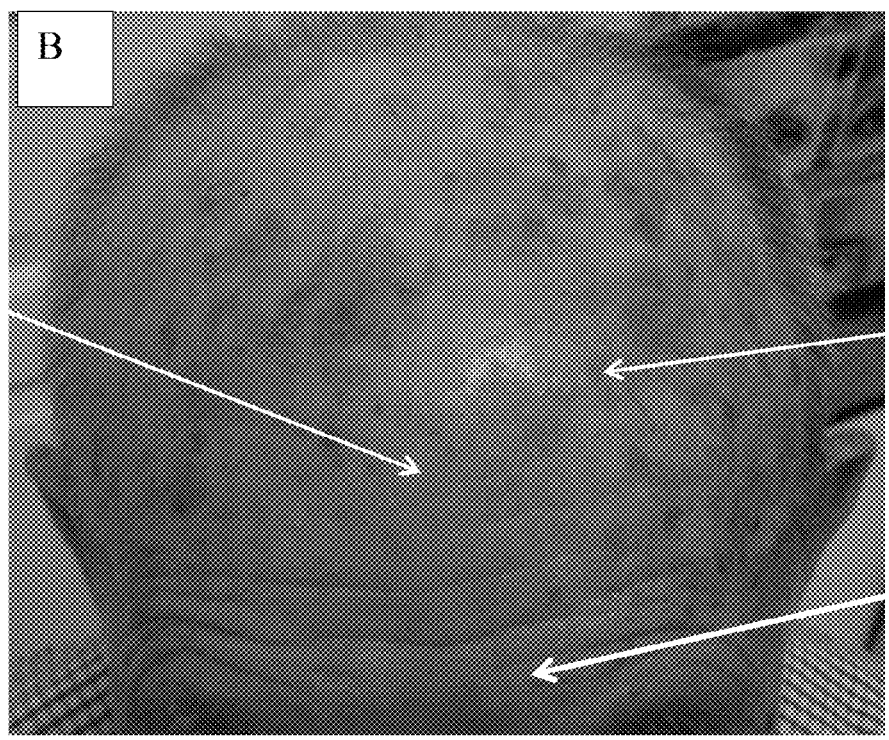

The present invention is directed to methods and compositions for the treatment or prevention of actinic keratosis and/or for countering the effects of sun-induced damages and/or damage to blood vessels. The present invention is based, at least in part, on the surprising discovery that a composition comprising aluminum fluoride or chemical compounds which finally release aluminum fluoride can be used to treat or prevent actinic keratosis or skin aging.

Aluminum Fluoride is an ubiquitous ingredient of toothpaste, widely and safely used for its anti cavity effects. Fluorides provide teeth and bone mineralization and are advocated by the health authorities (Palmer, Gilbert 2012). In addition, Aluminum fluoride has been identified and used in clinical trials as a beneficial agent for the treatment of pilosebaceous gland inflammations, in particular, acne vulgaris (U.S. Pat. No. 7,452,556). However, the inflammatory pathophysiology of acne (Williams et al, 2012) is highly distinct from the hyperproliferative precancerous actinic keratosis. In particular, acne vulgaris and folliculitis are inflammatory diseases of the pilosebaceous glands which are related to hormonal changes. As a result, such inflammations affect younger subjects in which hormonal changes are more prominent.

In contrast, actinic keratosis is induced by ultraviolet radiation in genetically susceptible subjects and, as a result, it affects the middle-aged and elderly. Thus, the present invention surprisingly has found that the use of aluminum fluoride is effective in treating actinic keratosis that is likely to affect older subjects, that being, over 30 years old.

Notably, the oral ingestion of fluoride salts, but not specifically aluminum fluoride, has been implicated in the past as relevant to cancers, being either detrimental, non-beneficial/non-detrimental, i.e. inactive, or beneficial to solid cancers. There is laboratory evidence implying fluorides as an etiology of bone cancer in animals or involved through epidemiological data. On the contrary, beneficial effects of all fluoride salts on solid tumors (US Patent Publication No. 2003/0170318 A1) were suggested. More recent epidemiological statistics suggests no influence, neither detrimental nor beneficiary, on cancer in humans (Kleerekoper 1994; Chilvers, 1983; Levy, Leclerc 2012)

Now, it has surprisingly found in the present invention that aluminum fluoride is an effective agent for actinic keratosis treatment. Actinic keratosis is induced by ultraviolet radiation in genetically affected or unaffected individuals, related to skin aging and, as a result, it affects epidermal cells in the middle-aged and elderly (Nouri, 2008). The results set forth below surprisingly demonstrate that aluminum fluoride acts as a highly effective drug for the treatment of AK.

Accordingly, the present invention provides compositions for the treatment or prevention of actinic keratosis or skin aging comprising aluminum fluoride and methods for such treatment comprising administering said compositions in a therapeutically effective amount to a subject.

As used herein, the term "actinic keratosis" refers generally to the art recognized condition, also known as solar keratosis, characterized by thick, scaly or crusty patches of skin, often in the form of lesions or microerosions, often surrounded by red, irritated skin. Such conditions can be found most commonly on sun-exposed areas such as the scalp, head, neck, hands or other areas of the body. The condition may be a premalignant disorder and may progress to squamous cell carcinoma. All forms of actinic keratosis are intended to be included by the term "actinic keratosis" including, but not limited to, actinic cheilitis, inflammatory keratosis, hypertrophic keratosis and pigmentary keratosis.

As used herein, the term "sun-induced damage" also includes damage to blood vessels and collagen, for example, arising from exposure to external elements such as ultraviolet irradiation, toxins and the sun.

As used herein, the term "aluminum fluoride" is intended to refer to the art recognized compound aluminum fluoride, also known as aluminum trifluoride or $AlF_3$ (CAS No 7784-18-1, EINECS No. 232-051-1).

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Unless specified otherwise, all values provided herein can be assumed to include the term about.

As used herein, the term "subject" includes warm-blooded animals, preferably mammals, including humans. In a preferred embodiment, the subject is a primate. In an even more preferred embodiment, the primate is a human.

As used herein, the terms "treat," "treatment" and "treating" include the application or administration of the compositions of the present invention, for example, aluminum fluoride compositions, to a subject who is suffering from actinic keratosis, sun damage, skin aging and/or damage to blood vessels and collagen or who is susceptible to such conditions with the purpose of curing, healing, alleviating, relieving, altering, remedying, ameliorating, improving or affecting such conditions or at least one symptom of such conditions. As used herein, the condition is also "treated" if recurrence of the condition is reduced, slowed, delayed or prevented.

As used herein, the term "administering" to a subject includes dispensing, delivering or applying a composition comprising aluminum fluoride or consisting of aluminum fluoride as a single active agent to a subject by any suitable route for delivery of the aluminum fluoride to the desired location in the subject, including delivery by topical application. Alternatively or in combination, delivery is by intramuscular injection, subcutaneous/intradermal injection, buccal administration, transdermal delivery, topical delivery. Preferably, the compositions of the invention are administered topically, e.g., to the skin of an affected subject.

As used herein, the term "sustained delivery" or "sustained release" is intended to refer to continual delivery of aluminum fluoride in vivo over a period of time following administration, preferably at least several days, a week or several weeks and up to a month or more. In a preferred embodiment, a formulation of the invention achieves sustained delivery for at least about 7, 14, 21 or 28 days, at which point the sustained release formulation can be re-administered to achieve sustained delivery for another 28 day period (which re-administration can be repeated every 7, 14, 21 or 28 days to achieve sustained delivery for several months to years). Sustained delivery of the aluminum fluoride can be demonstrated by, for example, the continued therapeutic effect of the aluminum fluoride over time. Alternatively, sustained delivery of the aluminum fluoride may be demonstrated by detecting the presence of the aluminum fluoride in vivo over time.

As used herein, the term "therapeutically effective amount" includes an amount effective, at dosages and for periods of time necessary, to achieve the desired result, e.g., sufficient to treat a subject suffering from actinic keratosis; sufficient to prevent actinic keratosis, for example, in a subject likely to develop actinic keratosis; sufficient to treat or alleviate skin aging and/or damage to blood vessels; or sufficient to prevent skin aging and/or damage to blood vessels and fine wrinkling, for example, in a subject predisposed to such conditions. An effective amount of aluminum fluoride, as defined herein may vary according to factors such as the state, severity and extent of the condition, i.e., actinic keratosis, sun damage, skin aging and/ or damaged blood vessels, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the aluminum fluoride are outweighed by the therapeutically beneficial effects.

The aluminum fluoride is present in the compositions in an amount effective to treat, for example, alleviate, or reduce the effects of actinic keratosis. Alternatively, the aluminum fluoride is present in the compositions in an amount sufficient to treat, for example, alleviate, or reduce the effects of sun induced damages and/or damage to blood vessels. The aluminum fluoride may be present in the compositions at a concentration of about 0.05% to about 2.00% w/w. Preferably, the aluminum fluoride may be present in the compositions at a concentration selected from the group consisting of about 0.10% to about 0.75% w/w, about 0.25% to about 0.60% w/w, about 0.30% to about 0.55% w/w and preferably about 0.30% to about 0.45% w/w. Ranges intermediate to the above recited amounts, e.g., about 0.08% to about 0.73% w/w, are also intended to be part of this invention. For example, ranges of values using a combination of any of the above recited values as upper and/or lower limits are intended to be included.

Alternatively or in combination, the aluminum fluoride may be present as a pharmaceutically acceptable salt. Moreover, alternatively or in combination, the composition may include chemical compounds which react or combine to form and release in vivo aluminum fluoride, for example a combination of aluminum and fluoride salts to achieve the desired therapeutic effect. Various fluoride embodiments, such as sodium monofluorophosphate, sodium fluoride and stannous fluoride are related to the present invention since they may release or combine with aluminum in a mixture. The compositions of the present invention may further include other agents, for example, inactive carriers. Inactive carriers including, but not limited to, deionized water, arachidyl alcohol, behenyl alcohol, arachidyl glucoside, montanov 202, cetearyl alcohol, capric caprilic triglyceride, isopropyl palmitate, steareth-2, dimethicon, steareth-20, allantoin, propylene glycol, methylisothiazolinone, Caprylic/Capric acids; medium chain, triglycerides, PEG 400, Pluronic F127, sodium benzoate, and combinations thereof may also be included. Moreover, the compositions of the invention may further include additional pharmaceutically and/or cosmetically acceptable compounds and/or compositions. Such as;

Oil in water or water in oil composition;

Surfactants such as anionic, e.g. ammonium lauryl sulfate or cationic e.g.

Cetylpyridinium chloride or nonionics e.g. Poloxamer F127, cetyl alcohol;

Emollients such as lanolin, glycerin, sorbitol or shea butter;

Thickening agents such as castor oil or polyethylene glycol;

pH stabilizers such as sodium citrate;

Antioxidants such as Vitamin C and E;

Fragrances as required; and

Preservatives such as parabens.

In a particular embodiment, the aluminum fluoride composition is suitable for topical administration and specifically applied to sunburned skin or skin affected and showing the effects of actinic keratosis due to ultraviolet radiation. For example, the composition may be in the form of a gel, liquid or spray to allow, for example, for topical application to lesions and scales associated with actinic keratosis. Alternatively, the composition may be in the form of a solution, lotion, mask, soap, moisturizer, powder, perfume, dye, brilliantine, aerosol, pomade, cream, ointment or paste.

The aluminum fluoride compositions of the present invention may be incorporated into pharmaceutical compositions suitable for administration to a subject, which allow for sustained delivery of the aluminum fluoride for a period of at least several weeks to a month or more. Preferably, the aluminum fluoride is the only active ingredient(s) formulated into the pharmaceutical composition, although in certain embodiments the aluminum fluoride may be combined with one or more other active ingredients including, but not limited to, retinoids, an anti-inflammatory agent, a non-steroidal anti-inflammatory agent, imiquimod, diclofenac, 5-aminolevulinic acid, 5-fluorouracil, and combinations thereof.

In one embodiment, the pharmaceutical composition comprises aluminum fluoride and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration or for administration via inhalation. Preferably, the carrier is suitable for topical administration, for example, to the skin. Alternatively, the carrier can be suitable for intramuscular or subcutaneous administration. In another embodiment, the carrier is suitable for oral administration. Pharmaceutically acceptable carriers include sterile aqueous solutions or dispersions and sterile powders for the extemporaneous preparation of sterile injectable solutions or dispersion. Supplementary active compounds can also be incorporated into the compositions.

The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prolonged absorption of the compositions can be brought about by including in the composition an agent which delays absorption, for example, monostearate salts and gelatin. Moreover, the compounds of the invention can be administered in a time release formulation, for example in a composition which includes a slow release polymer. The aluminum fluoride compositions can be prepared with carriers that will protect the aluminum fluoride against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers. Many methods for the preparation of such formulations are patented or generally known to those skilled in the art. The aluminum fluoride compositions can be formulated with one or more additional compounds that enhance the solubility of the aluminum fluoride.

The pharmaceutical formulation contains an effective amount of the aluminum fluoride. An effective amount of aluminum fluoride may vary according to factors such as the state of the actinic keratosis, skin aging or damage to blood vessels, age, and weight of the individual, and the ability of aluminum fluoride (alone or in combination with one or more other active agents) to elicit a desired response in the subject. Dosage regimens may be adjusted to provide the optimum therapeutic response. An effective amount is also one in which any toxic or detrimental effects of the aluminum fluoride are outweighed by the therapeutically or prophylactically beneficial effects.

In one embodiment, the aluminum fluoride may be co-administered to a subject along with another agent having therapeutic effect against actinic keratosis. Examples of such agents active against actinic keratosis include, but are not limited to, retinoids, an anti-inflammatory agent, a non-steroidal anti-inflammatory agent, imiquimod, diclofenac, azelaic acid, 5-aminolevulinic acid, 5-fluorouracil, and combinations thereof.

The composition according to the present invention may be topically applied as such within a suitable carrier, solvent, dissolvent, emulgent, extract, solutions e.g. aqueous, alcoholic, oily, suspension; microemulsion, vesicles, etc. Where employed, the carrier is inert in the sense of not bringing about a deactivation or oxidation of the aluminum fluoride, and in the sense of not bringing about any adverse effect on the skin areas to which it is applied.

In one aspect of the invention, at least one aluminum fluoride is applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin. While the aluminum fluoride carrier for dermatological compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration. Many preparations are known in the art, and include lotions containing oils and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids.

Various types of other ingredients may be present in compositions of the present invention. For example, sunscreens may be included such as those materials commonly employed to block ultraviolet light. Illustrative compounds are the derivatives of PABA, cinnamate and salicylate. The exact amount of sunscreen employed in the compositions can vary depending upon the degree of protection desired from the sun's UV radiation.

The compositions for use in the methods of the present invention may include components such suitable carriers such as starches, emollients, sugars, alcohols, microcrystalline cellulose, diluents, granulating agents, lubricants, surfactants including amphoteric, binders, disintegrating agents, and the like, with the topical preparations being preferred.

Emollients are often incorporated into the therapeutic compositions of the present invention. Levels of such emollients may range from about 0.5% to about 60% w/w, preferably between about 5% and 30% by weight of the total composition. Emollients may be classified under such general chemical categories as esters, fatty acids and alcohols, polyols and hydrocarbons. Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Suitable fatty alcohols and acids include those compounds having from 10 to 20 carbon atoms. Especially preferred are compounds such as cetyl, arachidyl, behenyl, cetearyl, myristyl, palmitic and stearyl alcohols and acids. Among the polyols which may serve as emollients are linear and branched chain alkyl polyhydroxyl compounds. For example, propylene glycol, resorcinol, menthol, bisabolol, sorbitol and glycerin are preferred. Also useful may be polymeric polyols such as polypropylene glycol and polyethylene glycol. Exemplary hydrocarbons which may serve as emollients are those having hydrocarbon chains anywhere from 12 to 30 carbon atoms. Specific examples include mineral oil, lanolin, shea butter, petroleum jelly, paraffin oil, squalene and isoparaffins.

Another category of functional ingredients within the therapeutic compositions of the present invention are thickeners. A thickener will usually be present in amounts anywhere from 0.1% to 20% w/w, preferably from about 0.5% to 10% by weight of the composition. Exemplary thickeners are cross-linked polyacrylate materials. Gums may be employed such as xanthan, carrageenan, gelatin, karaya, pectin and locust beans gum. Under certain circumstances the thickening function may be accomplished by a material also serving as a silicone or emollient. For instance, silicone gums having a viscosity in excess of 10 mPas and esters such as glycerol stearate have dual functionality.

Still further, the therapeutic compositions of the present invention may include preservatives, moisturizers, surfactants, antimicrobials, etc. Preservatives may include tetrasodium ethylene-diamine tetraacetic acid (EDTA), methylparaben, benzophenone-4, methylchloroisothiazolinone, sodium benzoatemethylisothiazolinone, and the like, and mixtures thereof. Preservatives, when used, are typically present in an amount from about 0.01% to 10% weight, preferably about 0.05% to 4% weight, and more preferably, from about 0.1% to 2% weight.

The inclusion of moisturizers may include wheat protein (e.g., laurdimonium hydroxypropyl hydrolyzed wheat protein), hair keratin amino acids, sodium peroxylinecarbolic acid, panthenol, tocopherol (Vitamin E), dimethicone, arachidylglucoside and the like, and mixtures thereof. Moisturizers, when used, are typically present in an amount from about 0.01% to 10% weight, preferably about 0.05% to 1.5% weight, more preferably, from about 0.1% to 1% weight of the composition.

Acceptable surfactants, including both the foaming and non-foaming type, include sodium laureth sulfate, sodium laureth-13 carboxylate, disodium laureth sulfosuccinate, disodium cocoamphodiacetate, glycol stearate, PEG-150 distearate and the like, and mixtures thereof. The surfactant component may be present in an amount from about 0.1% to about 20% weight of the composition.

Any pharmaceutically acceptable antimicrobial agent available to those of ordinary skill in the art may be used in the present compositions including: echinacea, golden seal, benzalkonium chloride, triclosan, benzethonium chloride, iodine, grape seed extract, pomegranate extract, green tea extract or polyphenols, and the like, or combinations thereof. The antimicrobial agent is typically present in an amount from about 0.01% to 2% weight, preferably from about 0.1% to 1.2% weight, and more preferably from about 0.3% to 1% weight of the composition. The antimicrobial agent inhibits the formation, and may further reduce, the presence of microbes that cause redness, inflammation, and irritation of the skin.

The topical skin treatment composition of the invention can be formulated as a lotion having a viscosity of from 4,000 to 10,000 mPas, a fluid cream having a viscosity of from 10,000 to 20,000 mPas or a cream or a gel having a viscosity of from 20,000 to 100,000 mPas or above.

The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

Generally, in the practice of methods of the invention, the composition is topically applied to the affected skin areas in a predetermined or as-needed regimen either at intervals by application of a lotion or the like, it generally being the case that gradual improvement is noted with each successive application. For example, in use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Because of its ease of administration, a cream, lotion, gel or ointment represents the most advantageous topical dosage unit form, and such forms may be prepared as rinse-off or leave-on products, as well as two stage treatment products for use with other skin cleansing or managing compositions. Each of these forms is well understood by those of ordinary skill in the art, such that dosages may be easily prepared to incorporate the pharmaceutical composition of the invention.

The present invention is further directed, in part, to methods of treatment and/or prevention of actinic keratosis by administering to a subject an effective amount of a composition comprising aluminum fluoride, a pharmaceutically acceptable salt thereof, or a combination of compounds which allow for the release of aluminum fluoride in vivo, thereby treating and/ or preventing actinic keratosis.

The compositions of the present invention may be administered as necessary to achieve the desired effect and depend on a variety of factors including, but not limited to, the severity of the condition, age and history of the subject and the nature of the composition, for example, concentration of aluminum fluoride and/or sustained release capabilities. In various embodiments, the compositions may be administered at least two, three, four, five or six times a day. Additionally, the therapeutic or preventative regimens may cover a period of at least 1 to 24 weeks.

The effectiveness of the treatments described herein can be assessed based on a variety of factors including, for example, the disappearance of lesions, microerosions and/or scales; a reduction in size and/ or severity of the lesions, microerosions and/or scales; and/ or a reduction of the number of lesions, microerosions and/or scales.

In certain embodiments, the methods of the present invention involve co-administration of aluminum fluoride, a pharmaceutically acceptable salt thereof, or a combination of compounds which release aluminum fluoride in vivo, with an additional active agent including, but not limited to, retinoids, an anti-inflammatory agent, a non-steroidal anti-inflammatory agent, imiquimod, diclofenac, a, 5-fluorouracil, 5-aminolevulinic, azelaic acid, other agents having therapeutic or preventative effect against actinic keratosis and combinations thereof.

Additionally, the methods of the present invention further include performing a procedure on a subject for removing lesions, scales and/or microerosions associated with actinic keratosis including, but not limited to, cryotherapy, excision, curettage, electrodesiccation, electrocautery, photodynamic therapy and laser therapy.

Subjects suitable for treatment using the regimens of the present invention should have or are susceptible to developing actinic keratosis. Actinic keratosis can be diagnosed through routine skin examinations, for example, through use of a bright light or magnifying lens. Additionally, skin biopsies may be performed to confirm the diagnosis.

Accordingly, in one aspect, the invention is directed to a method of treating or preventing actinic keratosis in a subject by selecting a subject who is susceptible to the development of actinic keratosis and administering to the subject an effective amount of a composition comprising aluminum fluoride, a pharmaceutically acceptable salt thereof, or a combination of compounds to allow for the release of aluminum fluoride in vivo, thereby treating or preventing actinic keratosis in the subject. As set forth above, in various embodiments, the subject may be older than about 30, 35, 40, 45, 50, 55, 60, 65 and 70 years old, may have had excessive exposure to the sun or ultraviolet irradiation, may live in a warm weather area and/or may have type I or II skin.

The present invention is further directed, in part, to methods of treatment and prevention of skin aging and damage to blood vessels by administering to a subject an effective amount of a composition comprising aluminum fluoride, a pharmaceutically acceptable salt thereof, or a combination of compounds which allow for the release of aluminum fluoride in vivo, thereby treating or preventing skin aging and/or damage to blood vessels and fine wrinkling.

As above with respect to treatment and prevention of actinic keratosis, the compositions of the present invention may be administered as necessary to achieve the desired effect. Accordingly, the regimen of administration depends on a variety of factors including, but not limited to, the severity of the condition, age and history of the subject and the nature of the composition, for example, concentration of aluminum fluoride and/or sustained release capabilities. In various embodiments, the compositions may be administered at least two, three, four, five or six times a day. Additionally, the therapeutic or preventative regimens may cover a period of at least 1 to 24 weeks with effective results usually shown in 3 to 4 weeks.

Monitoring the effectiveness of treatment may be achieved, for example, by measuring the intensity of blood vessels, measuring pigmentation and/ or measuring skin vascularization or fine wrinkling in the subject.

Subjects suitable for treatment using the regimens of the present invention may have or be susceptible to skin aging and/ or damage to blood vessels. Sun-induced damage and damage to blood vessels can be diagnosed through routine skin examinations, by measuring the intensity of blood vessels, measuring pigmentation and/ or measuring skin vascularization and fine wrinkling in a subject.

In addition, subjects susceptible and predisposed to skin aging, for example, intrinsic and/or extrinsic aging, can be identified by consideration of a variety of factors. For example, older subjects who are at least 30, 35, 40, 45, 50, 55, 60, 65 and 70 years old are susceptible to sun-induced damage and damage to blood vessels are suitable candidates for the methods of the present invention. Additionally, subjects who have had excessive exposure to the sun and/or ultraviolet irradiation, for example, subjects who live in warm weather areas, are particularly susceptible to skin aging and damage to blood vessels and fine wrinkling Moreover, subjects who are Caucasian or who have type I or II skin are particularly prone to skin aging and damage to blood vessels and fine wrinkling Accordingly, the invention is directed to a method of treating or preventing skin aging and/or damage to blood vessels in a subject by selecting a subject who is susceptible to the skin aging and/or damage to blood vessels and administering to the subject an effective amount of a composition comprising aluminum fluoride, a pharmaceutically acceptable salt thereof, or a combination of compounds to allow for the release of aluminum fluoride in vivo, thereby treating or preventing skin aging and/or damage to blood vessels and fine wrinkling in the subject. As set forth above, in various embodiments, the subject may be older than about 30, 35, 40, 45, 50, 55, 60, 65 and 70 years old may have had excessive exposure to the sun or ultraviolet irradiation, may live in a warm weather area and/or may have type I or II skin.

This invention is further illustrated by the following examples which should not be construed as limiting.

EXAMPLES

Example 1

FIGS. 1A and 1B depict the actinic keratosis lesions of Patient 1, a patient in his 8th decade, prior to and after 3 weeks. A cream was applied on dry skin, on the whole forehead, twice daily. Aluminum fluoride at 0.30% w/w was used in a base cream containing Caprylic/Capric acids, sulfur, resorcinol, medium chain triglycerides, PEG 400, Pluronic F127, Ylang ylang oil and water. It can be seen in Figure 1B that gradual disappearance of lesions is noted at 3 weeks of use.

Example 2

Figure 2:
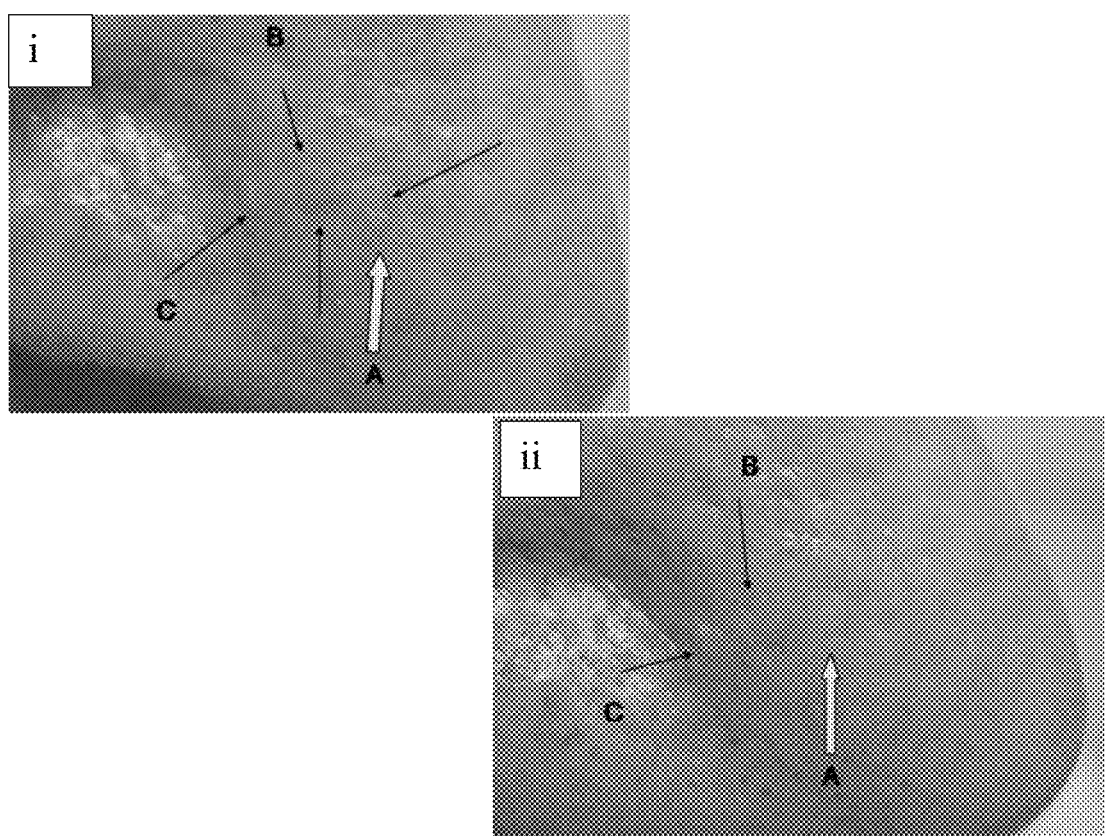
FIG. 2 show the effects of using AlFl at a dose of about 0.30%, daily for four weeks wherein A is before and B is after.

Patient 2 is a 48 year old female having actinic keratosis on her nose, in particular, two ulcers of about 1 mm each. The aluminum fluoride composition was at 0.30% w/w, and the base cream was modified to a cream containing deionized water, arachidyl alcohol, behenyl alcohol, arachidyl glucoside, montanoV 202, cetearyl alcohol, capric/caprilic triglyceride, isopropyl palmitate, steareth-2, dimethicon, steareth-20, allantoin, propylene glycol, Methylisothiazolinone (sheromix MT) and sodium benzoate. Application of the aluminum fluoride composition twice daily resulted in closure of the first ulcer and disappearance of the second ulcer after approximately three weeks. A major decrease in vascularization is noted and shown in FIG. 2($ii$) when compared to FIG. 2($i$).

Example 3

Figure 3:
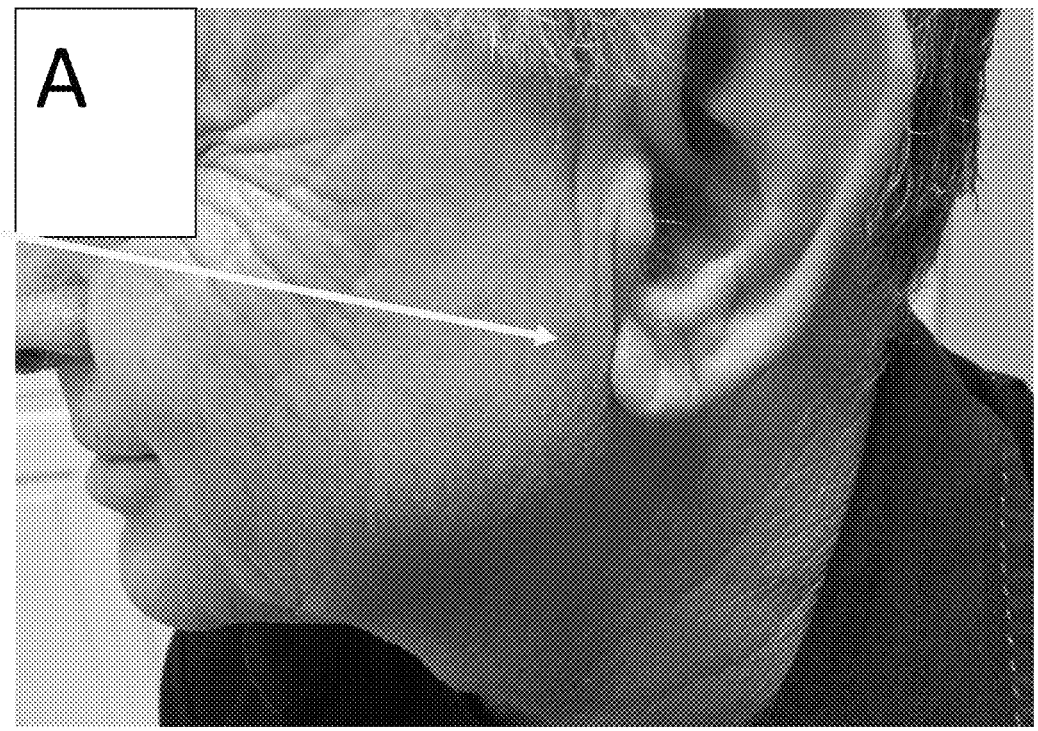
FIG. 3 show the effects of using AlFl at a dose of about 0.30%, twice daily for twelve weeks wherein A is before and B is after.
Figure 3:

FIGS. 3A and 3B depict the actinic keratosis lesions of Patient 6, a patient in his 6th decade, prior to and after 12 weeks of treatment. A cream was applied on dry skin, on the cheek, twice daily. Aluminum fluoride at 0.30% w/w was used in a base cream containing Caprylic/Capric triglycerides, a polyethylene glycol component, hydrophilic nonionic surfactant and purified water. It can be seen in FIG. 3B the disappearance of lesions is noted at 12 weeks of use.

Example 4

Figure 4:
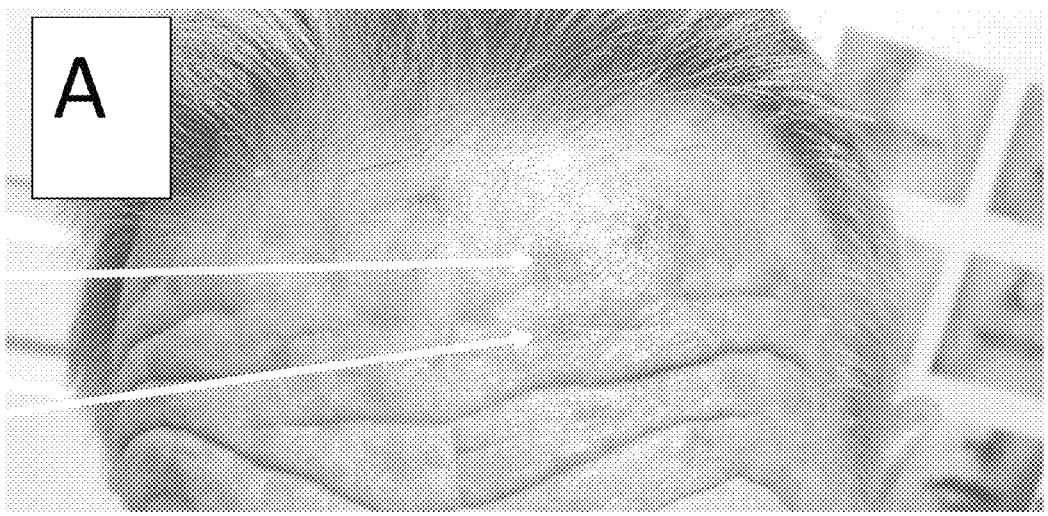
FIG. 4 show the effects of using AlFl at a dose of about 0.30%, twice daily for ten weeks wherein A is before and B is after.
Figure 4:
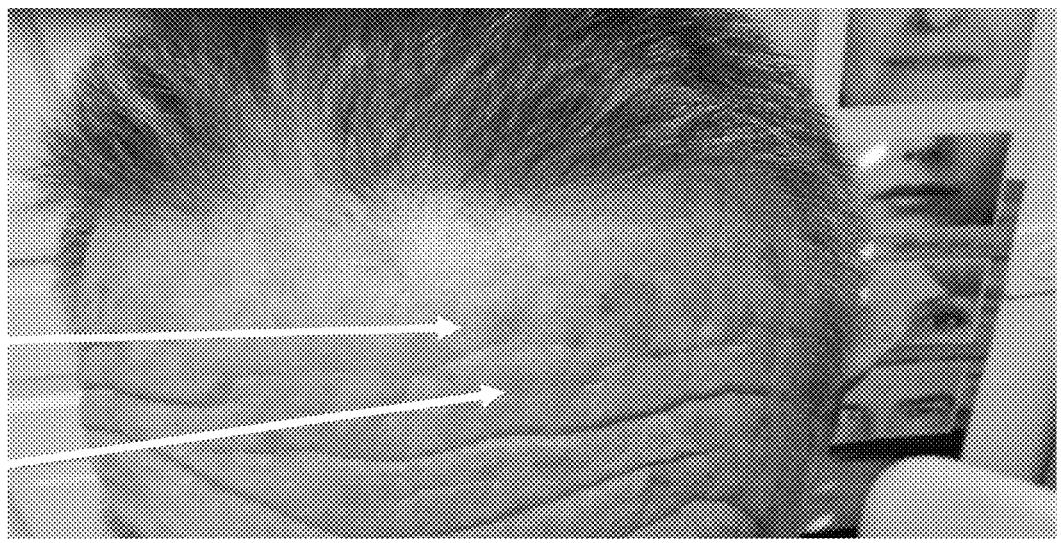

FIGS. 4A and 4B depict the actinic keratosis lesions of Patient 13, a patient in his 6th decade, prior to and after 10 weeks of treatment. A cream was applied on dry skin, on the whole forehead, twice daily. Aluminum fluoride at 0.30% w/w was used in a base cream containing Caprylic/Capric triglycerides, a polyethylene glycol component, hydrophilic non-ionic surfactant and purified water. It can be seen in FIG. 4B the disappearance of lesions is noted at 10 weeks of use.

REFERENCES

The contents of all references cited herein are incorporated by reference herein for all purposes.

Andrew's Diseases of the Skin. 9th Eds. Odom R E, James D J and Berger T G, eds. Saunders 2000. pp 810-12.

Chilvers C., *Int J Epidemiol*. Cancer mortality and fluoridation of water supplies in 35 US cities. 1983 December; 12(4):397-404.

Fenske N A, Spencer J, Adam F. Actinic keratoses: past, present and future. *J Drugs Dermatol*. 2010 May; 9 (5 Suppl ODAC Conf Pt 1):s45-9.

Kleerekoper M., *Adv Dent Res*., Non-dental tissue effects of fluoride. 1994 June; 8(1):32-8.

Levy M, Leclerc B S., Cancer Epidemiol. Fluoride in drinking water and osteosarcoma incidence rates in the continental United States among children and adolescents. 2012 April; 36(2):e83-8.

Palmer C A, Gilbert J A; Position of the Academy of Nutrition and Dietetics: the impact of fluoride on health. *J Acad Nutr Diet*. 2012 September; 112(9):1443-53.

Skin Cancer. Ed. Nouri K. McGraw-Hill. 2008. pp 32-45.

Williams H C, Dellavalle R P, Garner S. Acne vulgaris. *Lancet*. 2012 Jan. 28; 379(9813):361-72.

That which is claimed is:

1. A method of treating actinic keratosis and its accompanying sun-induced damage the method comprising administering to a subject in need of such treatment a topical composition comprising aluminum fluoride, or a pharmaceutically acceptable salt thereof as a sole active agent, in a therapeutically effective amount from about 0.10% to about 0.75% per weight of the topical composition.

2. The method according to claim 1, wherein the actinic keratosis is actinic cheilitis, inflammatory actinic keratosis, solar keratosis, hypertrophic keratosis or pigmentary keratosis.

3. The method according to claim 1, wherein the topical composition is applied to the surface of skin experiencing the negative effects of actinic keratosis.

4. The method according to claim 1, wherein the therapeutically effective amount is from about 0.25% to about 0.60% per weight.

5. The method according to claim 1, wherein the aluminum fluoride based drug is combined with a pharmaceutical carrier to form a composition.

6. The method according to claim 1, wherein the topical composition is administered to said subject at least once, twice, three times, four times or five times a day.

7. The method according to claim 1, wherein the topical composition is administered to said subject over a period of 1 to 12 weeks.

8. The method according to claim 1, where the topical composition further comprises a carrier comprising at least two, three, four or five inactive ingredients selected from the group consisting of montanov 202, capric/caprilic triglyceride, isopropyl palmitate, methylisothiazolinone, sodium benzoate Caprylic/Capric acids; medium chain, triglycerides, PEG 400, PEG 3350, Poloxamer F127, and Pluronic F127.

9. A method for treating actinic keratosis, the method comprising administering to a subject in need of such treatment a topical composition comprising aluminum fluoride, or a pharmaceutically acceptable salt thereof, in a therapeutically effective amount from about 0.10% to about 0.75% per weight of the topical composition, wherein the actinic keratosis is actinic cheilitis, inflammatory actinic keratosis, solar keratosis, hypertrophic keratosis or pigmentary keratosis.

10. The method according to claim 9, wherein the topical composition is applied to the surface of skin experiencing the negative effects of actinic keratosis.

11. The method according to claim 9, wherein the aluminum fluoride is co-administered to a subject along retinoids, an anti-inflammatory agent, a non-steroidal anti-inflammatory agent, imiquimod, diclofenac, azelaic acid, 5-aminolevulinic acid, 5-fluorouracil, and combinations thereof.

12. The method according to claim 1, wherein the accompanying sun-induced damage includes proliferative blood vessels or fine wrinkling.

13. The method according to claim 9, wherein the accompanying sun-induced damage includes proliferative blood vessels or fine wrinkling.

\* \* \* \* \*